United States Patent [19]

Balsari et al.

[11] Patent Number: 5,177,016
[45] Date of Patent: Jan. 5, 1993

[54] MONOCLONAL ANTIBODY RECOGNIZING ANTHRACYCLINE GLYCOSIDE SPECIFIC EPITOPE AND HYBRIDOMA SECERNING THE ANTIBODY

[75] Inventors: Andrea Balsari; Maria I. Colnaghi; Mario Ghione, all of Milan, Italy

[73] Assignee: Istituto Nazionale per lo Studio e la Cura dei Tumori, Milan, Italy

[21] Appl. No.: 642,024

[22] Filed: Jan. 16, 1991

[30] Foreign Application Priority Data

Jan. 26, 1990 [IT] Italy ................... 19160 A/90

[51] Int. Cl.$^5$ .................. C12N 5/12; C07K 15/28
[52] U.S. Cl. .................. 435/240.27; 530/388.9
[58] Field of Search ............ 530/387, 389.9; 435/240.27

Primary Examiner—David L. Lacey
Assistant Examiner—Susan L. Futrovsky
Attorney, Agent, or Firm—Walter H. Schneider

[57] ABSTRACT

A monoclonal antibody against Doxorubicin and other anthracycline derivatives, being the monoclonal antibody able to selectively recognize epitopes located in correspondence or in proximity of the aromatic D ring of the anthracycline molecule, is described.

2 Claims, No Drawings

MONOCLONAL ANTIBODY RECOGNIZING ANTHRACYCLINE GLYCOSIDE SPECIFIC EPITOPE AND HYBRIDOMA SECERNING THE ANTIBODY

The present invention relates to a monoclonal antibody which is able to recognize specific anthracycline glycoside epitope and the hybridoma secerning said antibody.

Monoclonal antibodies against Doxorubicin have been already disclosed in EP-A-0316776 and in Int. J. Cancer 42:798-802, 1988.

The production of monoclonal antibodies against drugs, such as Doxorubicin and generally other antitumour anthracyclines, which are able to interfere with the immune system, turned out to be difficult, requiring the introduction of innovative procedures in the immunization process of the animals used as splenocyte source.

Particularly, it has been noticed that only resorting to a short immunization cycle and only in animals that were also subjected to another antigenic stimulus it is possible to induce the formation of splenocytes which can be fused to give monoclonal antibodies against Doxorubicin and Doxorubicin derivatives.

In the above-mentioned paper published in Int. J. Cancer the main features of a monoclonal antibody, abbreviated as MAD2, exhibiting a different affinity degree against several anthracycline derivatives, the highest affinity being anyway noticed against Doxorubicinol, a Doxorubicin metabolite, and Doxorubicin itself, are described in detail.

The availability of a monoclonal antibody recognizing different epitopes on the anthracycline molecule would allow the development of analytical methods for a whole class of substances and, moreover, would constitute a useful tool for the study of drug-receptor interactions, also including phenomena occurring as toxic or unwanted effects.

Said problems have been solved by the monoclonal antibody of the present invention, secreted by the hybridoma deposited at European Collection of Animal Cell Cultures (ECACC), PHLS Centre for Applied Microbiology & Research, Porton Down, Salisbury, Wilts, SP4, 0JG, U.K., on Jan. 10th, 1990, under accession number 90011003.

The antibody object of the invention, hereinafter also named with the abbreviation MAD11, which can be prepared with the same somatic hybridization already described for MAD2 antibody, is able to recognize different antigenic determinants, particularly the one located at the positions $C_4$–$C_5$ of the anthracyclinone residue, in contrast to the hitherto described antibody (MAD2) which recognizes the determinant constituted by positions $C_9$–$C_{11}$ of the Doxorubicin molecule, whose structural formula with relative numeration is hereinbelow reported:

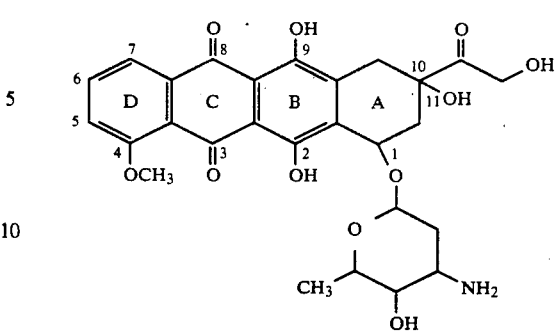

The ring D, which is 4-methoxy substituted, is a constant characteristic of almost all well-known anthracycline derivatives and this explains the wide recognition spectrum of the antibody of the invention. As already mentioned, such characteristic is advantageous for the above-mentioned aims.

The cross reactivity of MAD 11 was evaluated by inhibition tests, incubating (1 hour at 37° C.) a constant amount of antibody with different amounts of compounds structurally related to Doxorubicin. Then, the samples were incubated for 45 minutes at 37° C. in Doxorubicin coated wells and the binding was evaluated by adding $^{125}$I-radiolabelled mouse anti-Ig antibodies (Amersham Lab.). The curves, calculated as the mean value of at least 3 tests, resulted superimposable for Doxorubicin, Daunorubicin, Doxorubicinol, 5-imino-Doxorubicin, 11-deoxy-Daunorubicin, 4'-epi-Doxorubicin and 4'-deoxy-Doxorubicin. Instead it was noticed a substantially different inhibition behaviour for two compounds lacking of the 4-methoxy groups, namely Daunosamin and 4-demethoxy-Daunorubicin.

The antibody of the invention may be prepared according to the known procedure previously described for MAD 2 antibody.

50 μg of Doxorubicin-Bovine-Serum-Albumine (BSA) conjugate emulsified with complete Freund's adjuvant were injected in BALB/c mice, (previously conditioned by an unrelated antigen), at day 0 and 15 by subcutaneous route. On day 25, (i.e. three days before the fusion) a third administration of the conjugate at the same dose was carried out intra-peritoneally.

Cell fusion was accomplished using immunized spleen cells and mouse myeloma $P_3$/NSO cells with 40% (v/v) polyethylene glycol Mr 1000 (Merck, Darmstadt, West Germany).

Growing hybridomas were tested for immunoglobulin production using immunofluorescence (IF) assay as reported in Cancer Res. 43:1295-1300, 1983. The Ig containing supernatants were screened for anti-Doxorubicin antibody by a RIA technique on 96-well plates seeded with 50 μl/well of Doxorubicin ($2.5 \times 10^{-6}$M) or BSA as negative controls, diluted in carbonate buffer (pH 9.6). Sodium phosphate buffer (pH 7.2) (PBS) supplemented with Tween 20 (0.05%) was used as diluting and washing buffer.

The antibodies producing hybridomas which reacted with Doxorubicin but not with BSA alone were cloned by the method of limiting dilution and subsequently expanded in BALB/c mice primed with pristane (tetramethylpentadecane).

The antibody isolated from hybridoma N. 90011003 was purified by affinity chromatography on a Protein- A-Sepharose CL4B (Pharmacia) column as described by EY et al (Immunochem. 15, 429–436, 1978).

The antibody, eluted at pH 5.5, after dialysis against PBS was subjected to radiolabelling by lactoperoxidase-catalysed iodination. 1 mCi CiNa$^{125}$I (Amersham International, Little Chalfont, UK), 24 μg of lactoperoxidase (Calbiochem, Behring, La Jolla, Calif.) and 8 μl of 0.03% $H_2O_2$ were added to 50 μg of monoclonal antibody. After 10 minutes at room temperature the reaction was stopped by desalting the mixture on a Bio Gel Pg column (Bio Rad, Richmond, Calif.).

The labelled antibody was titrated by serial dilution ($10^6$ to 7800 cpm/well) on Doxorubicin coated wells, incubating for 3 hours at 4° C.

An affinity value of the antibody of $1.7 \times 10^{-8} M^{-1}$, was obtained by scatchard analysis.

The antibody MAD 11 was shown to belong to the IgG2 class unlike the antibody MAD2 which belongs to the IgG1 class, as resulted from direct immunofluorescence assay on hybridoma cells.

We claim:

1. Monoclonal antibody which specifically binds anthracycline glycosides belonging to subclass IgG2 secreted by the hybridoma deposited at European Collection of Animal Cell Cultures (ECACC) under N. 90011003.

2. Hybridoma deposited at European Collection of Animal Cell Cultures (ECACC) under N. 90011003.

* * * * *